United States Patent [19]

Esser

[11] Patent Number: 5,601,550

[45] Date of Patent: Feb. 11, 1997

[54] PELVIC PIN GUIDE SYSTEM FOR INSERTION OF PINS INTO ILIAC BONE

[76] Inventor: Rene D. Esser, 881 Lurline Dr., Foster City, Calif. 94404

[21] Appl. No.: 329,068

[22] Filed: Oct. 25, 1994

[51] Int. Cl.$^6$ .................................................. A61B 17/56
[52] U.S. Cl. ................................. 606/54; 606/80; 606/96
[58] Field of Search .................................. 606/96, 98, 86, 606/104, 80, 79

[56] References Cited

U.S. PATENT DOCUMENTS

| | | | |
|---|---|---|---|
| 4,292,964 | 10/1981 | Ulrich . | |
| 4,570,624 | 2/1986 | Wu | 606/96 |
| 4,708,139 | 11/1987 | Dunbar, IV | 606/96 |
| 4,848,327 | 7/1989 | Perdue . | |
| 5,163,940 | 11/1992 | Bourque | 606/96 |

FOREIGN PATENT DOCUMENTS

| | | | |
|---|---|---|---|
| 681828 | 10/1939 | Germany | 606/96 |
| 681829 | 10/1939 | Germany | 606/96 |
| 839510 | 6/1981 | U.S.S.R. | 606/96 |

*Primary Examiner*—Guy V. Tucker
*Attorney, Agent, or Firm*—James W. Pravel

[57] ABSTRACT

A pelvic drill guide apparatus is used to insert external fixation pins into a patient's pelvis that is fractured (for example as a result of trauma such a automobile roll-over) in "open book" fracture fashion. Multiple fixation pins are placed into the pelvis on each side (for example 2 pins on each side). An external fixation frame holds the pins and thus the pieces of the pelvis together. The guide apparatus includes an elongated probe to track the surface of the pelvis at the inner table of the pelvis. A barrel portion of the guide apparatus tracks a drill to form surgical openings that begin at the iliac crest. The drill path is off-set slightly with respect to the tip of the probe so that the surgeon can drill holes in the pelvis with minimal invasion.

15 Claims, 6 Drawing Sheets

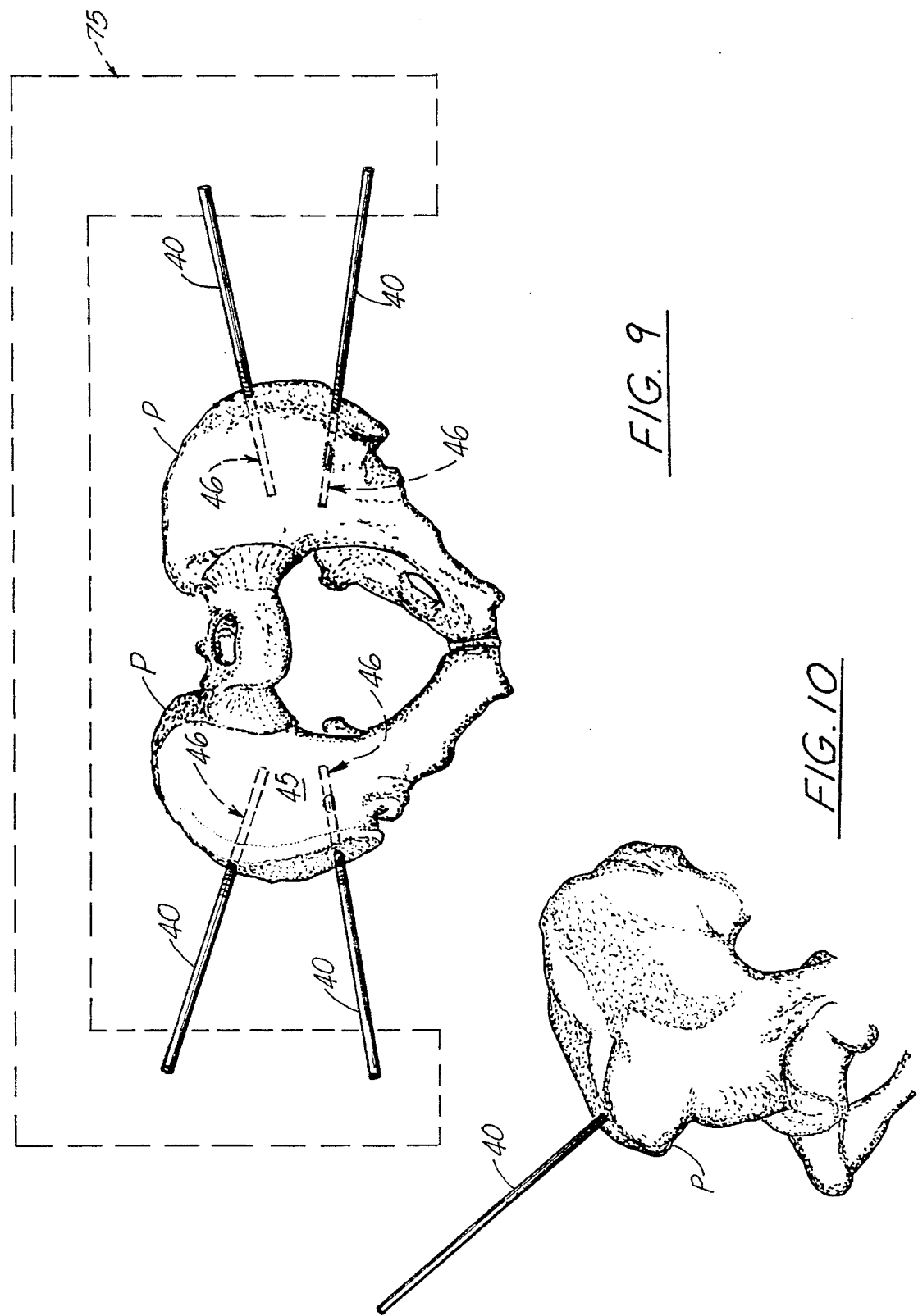

PELVIC PIN GUIDE SYSTEM FOR INSERTION OF PINS INTO ILIAC BONE

BACKGROUND OF THE INVENTION

1. Field of the Invention

The present invention relates to orthopedic surgical instruments, and more particularly to a guide system for insertion of pins into a patient's iliac bone when serious disruption of the pelvic ring occurs (eg. an automobile accident) requiring stabilization with an external fixation device in the early stages of treatment, and wherein the guide system facilitates the insertion of pins into the iliac bone and shortens the time for surgery, independently of the external fixation system used.

2. General Background

When serious disruption of the pelvic ring occurs stabilization with an external fixation device can be of great benefit to the patient in the early stages of treatment. Blood loss is reduced by prompt application of an external fixation device.

SUMMARY OF THE PRESENT INVENTION

The present invention provides a system for the insertion of pins into a patient's iliac bone after injury that creates disruption of the pelvic ring. As a pre-operative preparation, the patient is placed in the supine position on an image intensification table. Image intensification may be used to confirm reduction and proper placement of fixator pins. The pelvis must be relatively reduced prior to incision to avoid undo tissue tension at the pin sites.

A small incision (for example 2 centimeters) is made on either side of the pelvis, just proximal to the ASIS (Anterior Superior Iliac Spine) and exposing the iliac crest. The muscle is elevated medial to the iliac crest and the distal free tip portion of the guide apparatus of the present invention is inserted and pushed along the inner table of the pelvis. The guide instrument is then centered on the pelvic rim in such a manner that the pins can be inserted through the guide apparatus in an anteroposterior direction almost perpendicular to the plane of the operating room table.

A drill guide is inserted into the instrument barrel bore. A pilot hole is drilled through the cortex of the iliac crest into the iliac bone. The guide prevents inadvertent penetration of either cortex from occurring. After withdrawal of the drill bit, a fixation pin is manually inserted through the guide apparatus using a T-wrench for example. A second pilot hole is drilled in a similar fashion and a second fixation pin is inserted using a T-wrench for example. This similar procedure is performed on the contralateral ilium. In emergency applications, both sides can be done simultaneously by two surgeons, to expedite pin placement.

With the four pins in place, an external fixation system can be mounted to the pins for stabilizing the patient's fractured pelvis.

The present invention thus provides an improved guide system for insertion of pins into the iliac bone. The pelvic pin guide apparatus of the present invention includes an instrument body that has a handle for gripping and manipulating the instrument body during placement of surgically drilled holes and insertion of pins in the patient's pelvis.

The instrument body includes a tubular barrel with a central longitudinal bore, preferably cylindrically shaped. A pointer extends from the proximate end of the barrel and along a line that is generally parallel and off-set from the central longitudinal axis of the bore of the tubular barrel. The pointer is provided for tracking the surface of the inner table of the pelvis prior to the placement of surgically drilled holes that will accept fixation pins.

The pointer includes a distal tip portion that is off-set a few millimeters from the central longitudinal axis of the barrel and spaced away from the distal end of the barrel along a line that coincides with the central longitudinal axis of the barrel.

The bore is sized and shaped to hold an elongated drill. The pointer is positioned adjacent to the outer surface of the drill when the drill is extended fully through the barrel to the pointer tip. When the user places the free distal tip of the pointer in a desired position along the inner table of the pelvis, the user then knows that the drill will not out-crop during placement of the surgically placed openings that will carry the fixation pins. The drill will track a path that is slightly offset from the pointer tip and thus under the pelvic table surface when the pointer is engaged with the table surface. The barrel can provide a first larger bore for receiving one of a set of sleeves of various sizes, namely providing different internal diameter bores. Thus, the sleeve can removably fit the bore of the barrel, the sleeve having a sleeve bore that conforms to the outer surface of the drill during use.

In the preferred embodiment, the pointer is an elongated member that is affixed to the outer surface of the barrel.

The handle includes a strut that affixes to the outer surface of the barrel and extends laterally away from the barrel.

A distal end portion of the barrel is provided with teeth for gripping the patient's tissue at the pelvis when the surgeon is preparing to place surgically formed holes in the patient's pelvis.

The gripping surface of the distal end of the barrel can comprise a pair of circumferentially spaced teeth at the distal end of the barrel.

The handle and the pointer are spaced circumferentially about the barrel at opposed positions preferably about one hundred eighty degrees (180°) apart about the outer surface of the barrel.

The method of the present invention provides an improved method for inserting pins into the iliac bone of a patient. The surgical steps include the first step of forming an incision on the side of the patient's pelvis just proximal to the ASIS, exposing the iliac crest. Muscle is then elevated medial to the iliac crest.

The drill guide is used to track the drill into the patient's pelvis, through the cortex of the iliac crest and into the iliac bone along a path that prevents inadvertent penetration of either cortex.

The method preferably includes the placement of a plurality of drilled openings on spaced apart locations. The drill preferably occupies a position within the bore of the drill guide and the pointer extends to the distal end of the drill guide at a position adjacent the drill outer surface when the drill is extended to the distal end of the drill guide.

The surgeon places a plurality of pins respectively in the plurality of drilled openings and then mounts an external fixation system to the pins after placement in the surgically formed openings.

BRIEF DESCRIPTION OF THE DRAWINGS

For a further understanding of the nature and objects of the present invention, reference should be made to the following detailed description taken in conjunction with the accompanying drawings, in which like parts are given like reference numerals, and wherein:

FIG. 9 is a top view of the patient's pelvis illustrating placement of fixation pins and convention external fixation system using the method and apparatus of the present invention;

FIG. 10 is side view of the patient's pelvis illustrating the placement of a fixation pin using the method and apparatus of the present invention;

DETAILED DESCRIPTION OF THE PREFERRED EMBODIMENT

Figure 1:
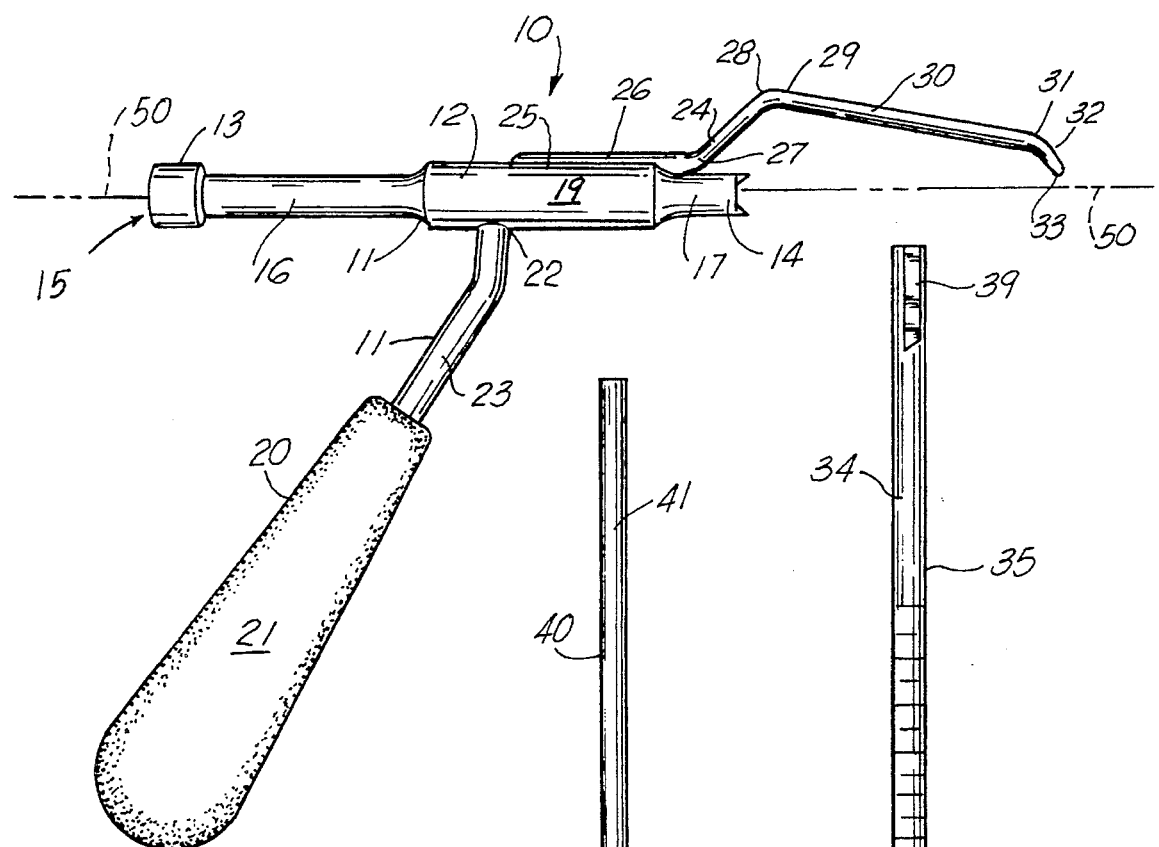
FIG. 1 is a side view of a first embodiment of the drill guide apparatus of the present invention.

FIGS. 1–3 and 6–7 illustrate a first preferred embodiment of the apparatus of the present invention designated generally by the numeral 10. Pelvic drill guide 10 includes an instrument body 11 that includes a barrel 12, handle 20 and a probe 24. Barrel 12 includes a proximal end 13 and distal end 14. Barrel 12 has a generally cylindrically shaped longitudinally extending, open ended bore 15 for receiving a drill during use.

Figure 7:
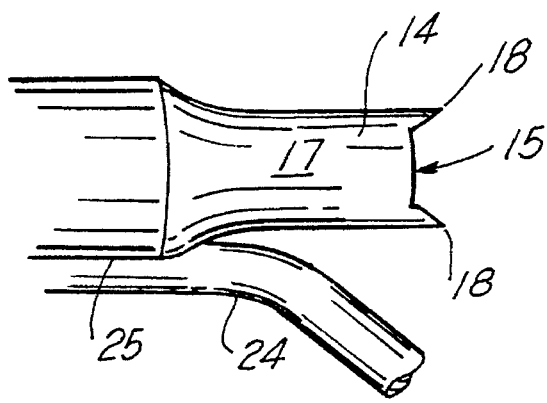
FIG. 7 is a partial perspective view of the guide apparatus of the present invention.
Figure 6:
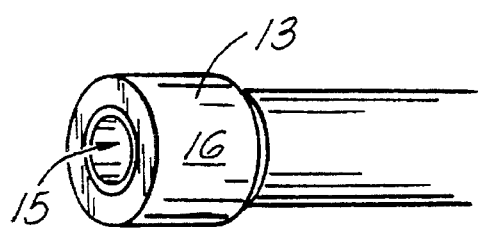
FIG. 6 is a partial perspective view of the first embodiment of the drill guide apparatus of the present invention.

Barrel 12 includes an enlarged central cylindrical portion 19 a smaller proximal cylindrical portion 16 and a smaller cylindrical portion 17 at distal end 14. Distal end 14 of barrel 12 carries a pair of teeth 18 that are circumferentially spaced about the smaller cylindrical portion 17 of barrel 12 as shown in FIG. 7. Teeth 18 project forward in a line that is generally parallel to the central longitudinal axis of bore 15.

Figure 4:
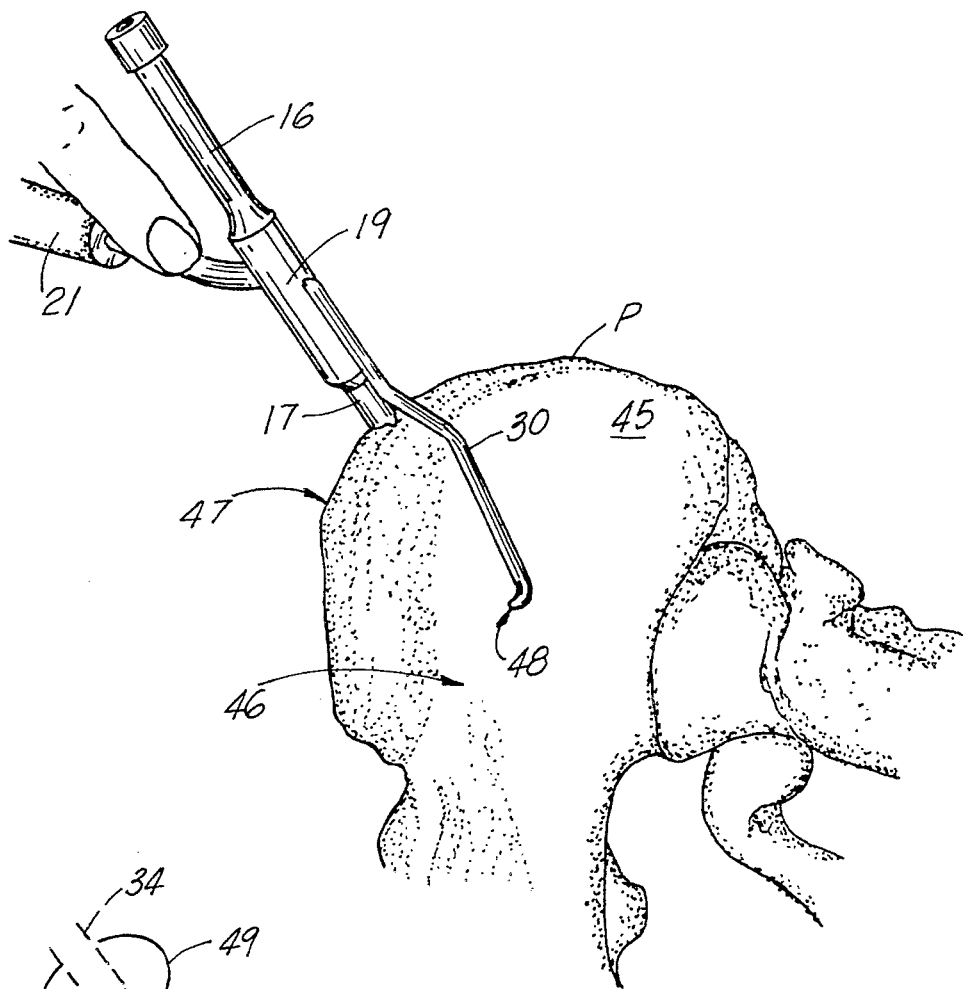
FIG. 4 is a perspective view illustrating the method of the present invention during placement of the drill guide at the patient's iliac crest and with the distal tip of the guide inserted and pushed along the inner table of the pelvis.

The teeth 18 are used to grip the patient's tissue at the pelvis as shown in FIG. 4.

The surgeon places the instrument body 11 in a desired position and then surgically forms drilled openings in the patient's pelvis. Barrel 12 includes enlarged section 19 to which is attached handle. The handle 20 includes a gripping surface 21 and arm 23 that extends between gripping surface 21 and enlarged portion 19 of barrel 12 at connection 22.

Elongated probe 24 of pelvic drill guide 10 includes a straight section 26 that is attached by welding for example to the outer surface of enlarged section 19 of barrel 12. The probe or tip 24 also includes a bend 27, straight section 28, bend 29, straight section 30, bend 31, and straight section 32. The probe 24 carries a pointed distal tip 33.

During use, the surgeon inserts the probe 24 along the inner table of the pelvis P until the teeth 18 engage the pelvic rim. The distal tip 33 is engaging the inner table of the pelvis and the teeth 18 of the barrel 12 engage the iliac crest. In this position (see FIG. 4), the surgeon can place a drill 34 into the central longitudinally extending bore 15 of barrel 12 to form surgically drilled openings in the patient's pelvis P.

Figure 2:
FIG. 2 is a side view of a drill for use with the drill guide apparatus of the present invention.

The drill 34 as seen is FIG. 2, can be generally cylindrically shaped, having a larger cylindrical portion 35, a smaller cylindrically shaped cutting portion 37, and an annular shoulder 36 positioned between the section 35, 37. The drill 34 includes a cutting distal tip 38 and a proximal end that includes a plurality of flats 39 for forming a connection between the drill 34 and a drill chuck (not shown).

Figure 3:
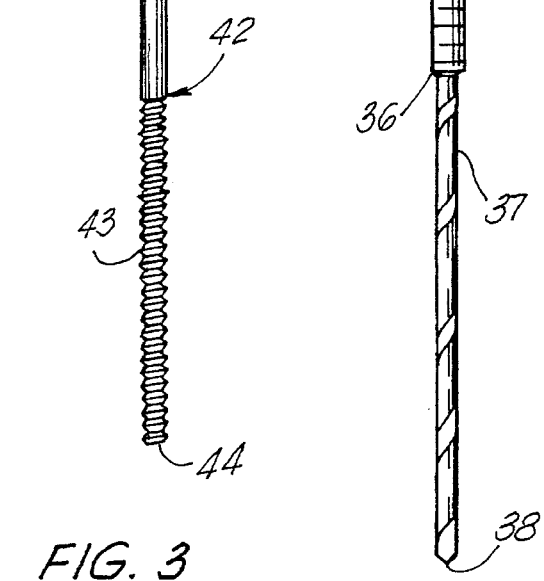
FIG. 3 is a side view of a fixation pin for use with the drill guide apparatus of the present invention and in the method of the present invention.

Once the surgeon forms a plurality of drilled openings in the patient's pelvis, a plurality of fixation pins 40 can be placed into those openings. An acceptable pin 40 is shown in FIG. 3 that includes a cylindrical unthreaded section 41, a helically threaded section 43, and a distal tip 44 that can define a self tapping thread. Arrow 42 indicates the position between the threaded and non-threaded sections 43,41.

In FIGS. 4–5 and 8–10 the method of the present invention is illustrated more particularly. In FIG. 4, the surgeon has placed instrument body 10 in proper position before inserting drill 34 into the bore 15 of barrel 12. In FIG. 4, the surgeon has already formed a small incision (for example two (2) centimeters) on the side of the pelvis just proximal to ASIS and exposing the iliac crest 47.

Figure 5:
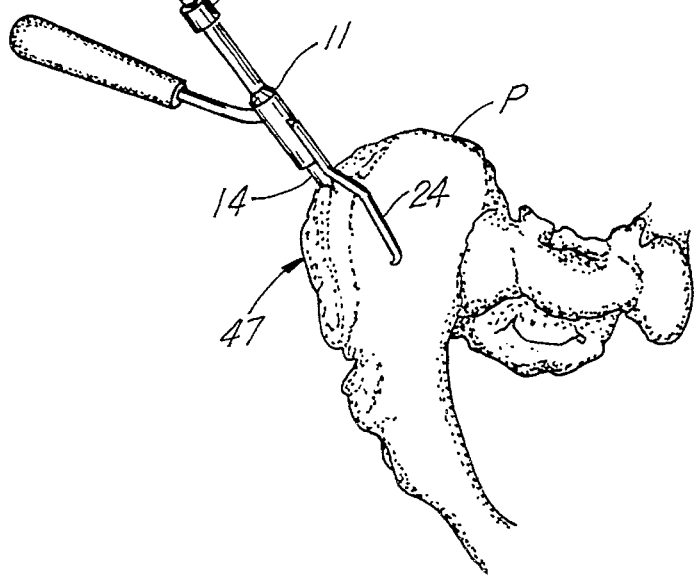
FIG. 5 is a perspective view of the first embodiment of the apparatus of the present invention and illustrating the method step of the present invention that includes surgical placement of a drilled opening in the patient's pelvis.
Figure 8:
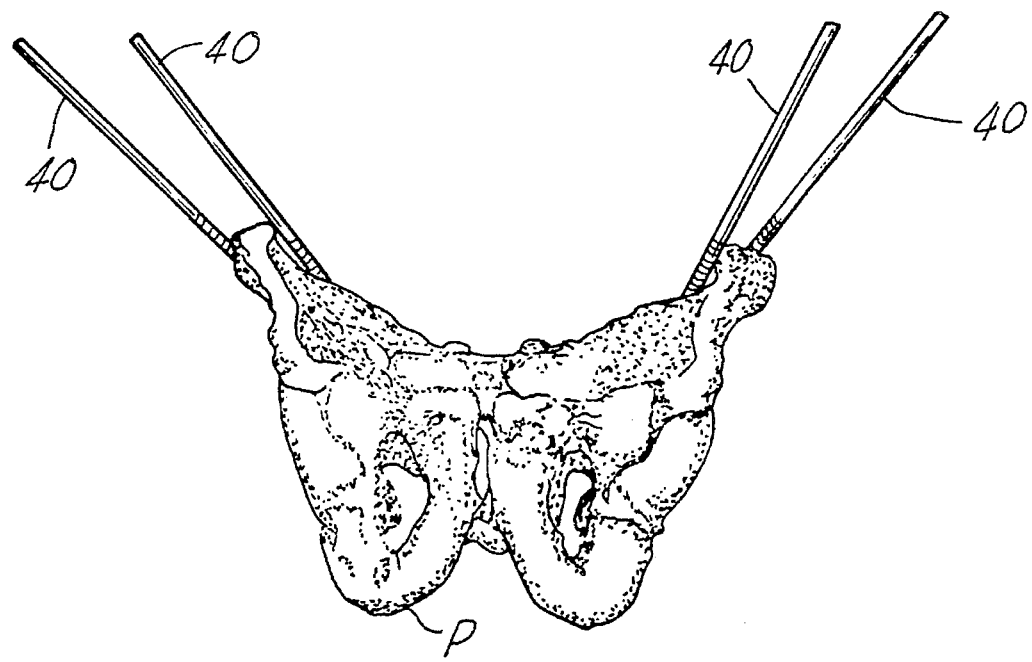
FIG. 8 is an anterior view of the patient's pelvis illustrating placement of a plurality of fixation pins using the method of the present invention.

The muscle is elevated medial to the iliac crest and the free tip 33 of guide apparatus 10 is inserted and pushed along the inner table 45 of the pelvis P. The guide apparatus 10 is centered on the iliac crest 47 in such a manner that pins 40 will be inserted in an anteroposterior direction almost perpendicular to the plane of the operating table. Drill 34 is inserted into bore 15 of barrel 12 as shown in FIG. 5 and a pilot hole is drilled through the cortex of the iliac crest into the iliac bone.

The guide apparatus 10 prevents inadvertent penetration of either cortex from occurring. After withdrawal of the drill 34 and guide apparatus 10, a fixation pin 40 is manually inserted using a T-wrench, for example. A second surgically formed pilot hole is drilled in a similar fashion and a second pin 40 is inserted again by means of a T-wrench, for example. In FIG. 9, the surgically formed openings are indicated in phantom lines by the numeral 46. The surgeon can then mount a conventional external fixation system 75 to the pins 40, as shown in FIG. 9.

In FIG. 1, the numeral 50 indicates the central longitudinal axis of the cylindrically shaped bore 15 that extends longitudinally through barrel 12. The pointed tip 33 is spaced a few millimeters (for example three (3) millimeters)

from the central longitudinal axis 50. This places the pointer tip 33 adjacent the outer surface of drill 34 at cylindrically shaped cutting portion 37.

By placing the tip 33 on the patient's inner table 45 (as shown in FIG. 4), at the position indicated by arrow 48 in FIG. 4, the surgeon insures that the drill will track into the patient's pelvis but not break through the surface 45 or outcrop inadvertently. Rather, the tip 33 is placed tightly against the surface 45 and the drill tracks under the surface 45. This insurance is provided by the geometry of the central longitudinal axis 50 being off-set with respect to the pointer tip 33.

Figures 11, 12:
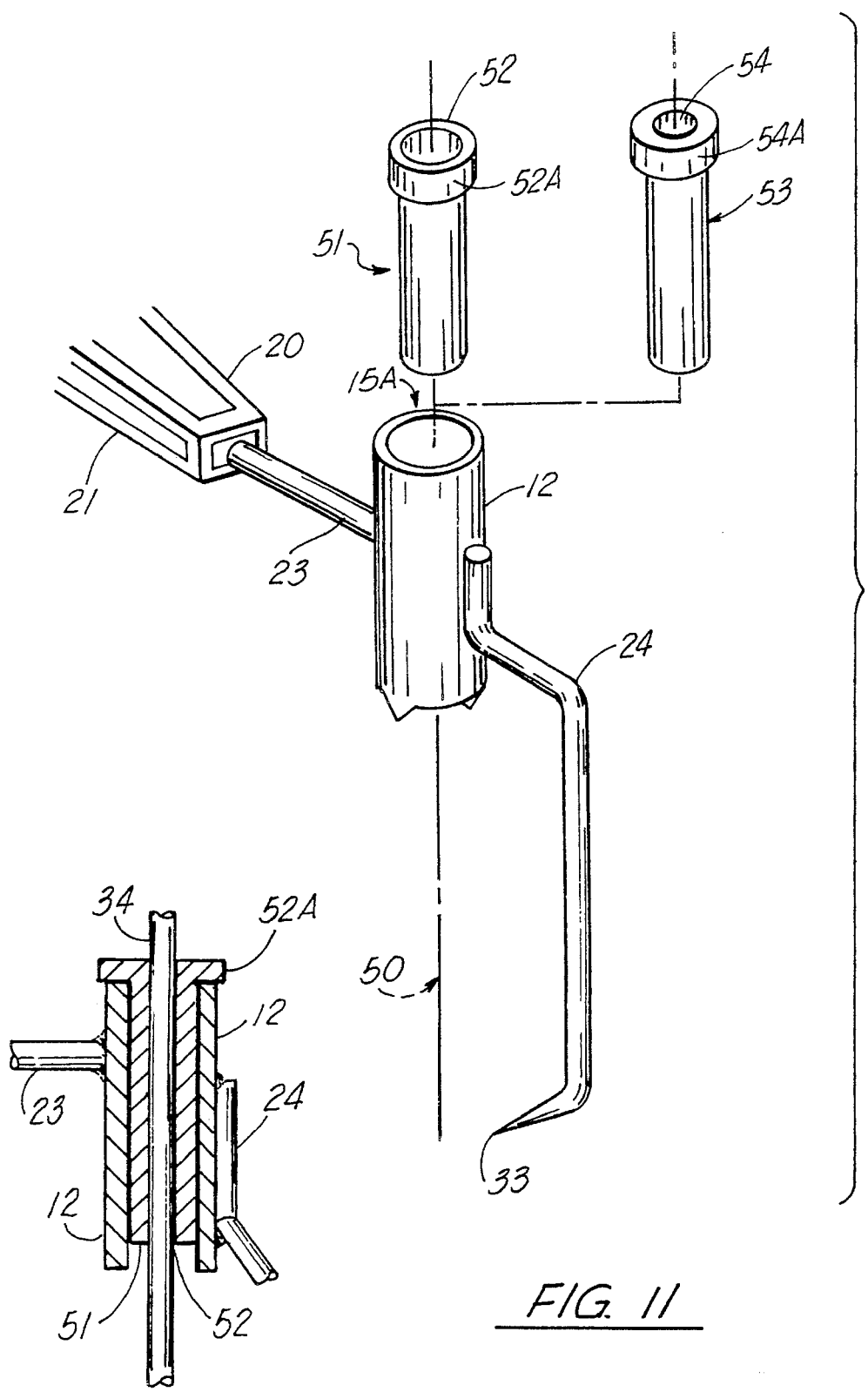
FIG. 11 is side view of a second embodiment of the apparatus of the present invention.
FIG. 12 is a sectional view of the second embodiment of the apparatus of the present invention.
Figure 13:
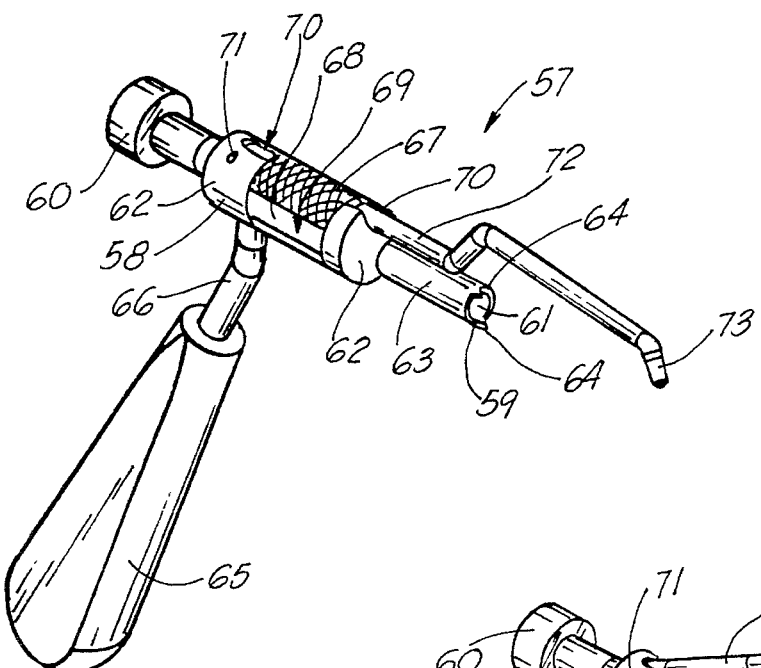
FIG. 13 is a perspective view of a third embodiment of the apparatus of the present invention.

In FIGS. 11–12, the barrel 12 has a bore 15A that is sized and shaped to receive interchangeable sleeves 51, 53 each having an internal sleeve bore 52,54 respectively. This allows different diameter drills 34 to be used with the same instrument body 11. Each sleeve 51, 53 has a large cylindrical collar 52A, 54A respectively that acts as a stop (see FIG. 12) when sleeve 51, 53 occupies bore 15A of barrel 12.

FIGS. 13–16 illustrate a third embodiment of the apparatus of the present invention designated generally by the numeral 57. Drill guide apparatus 57 provides an instrument body 58 having a distal end 59 and a proximal end 60. As with the first and second embodiments, a longitudinally extending open ended bore is provided for receiving a drill during use. The method of the present invention is the same with the embodiment of FIGS. 13–16 as with the embodiments of FIGS. 1–12. However, in the embodiment of FIGS. 13–16, a locking collar is provided for locking a probe in position wherein the probe pivots about the instrument body 58. Instrument body 58 includes a larger cylindrical section 62 and a smaller cylindrical section 63. Smaller cylindrical section 63 carries a pair of teeth 64 at distal end 59 of the apparatus 57. The apparatus 57 is supported using handle 65 that is connected with strut 66 to instrument body 58.

Figure 14:
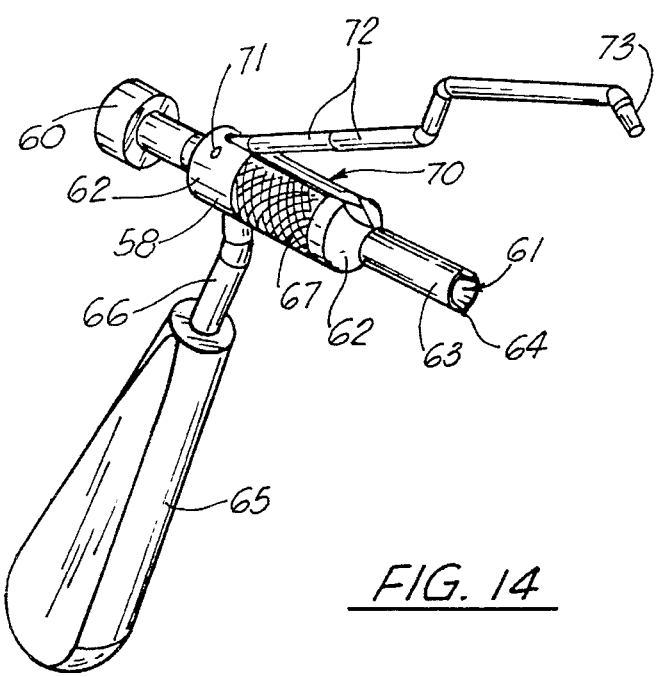
FIG. 14 is a perspective view of the third embodiment of the apparatus of the present invention, showing the probe in unlocked position.
Figure 15:
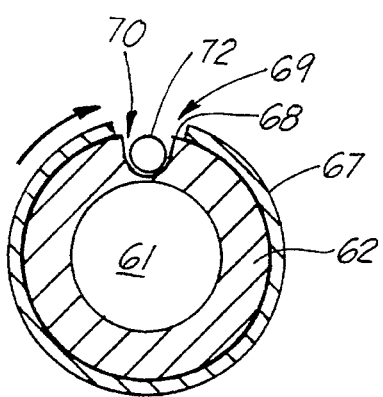
FIGS. 15–16 are sectional fragmentary views of the third embodiment of the apparatus of the present invention illustrating the probe and locking collar.
Figure 16:
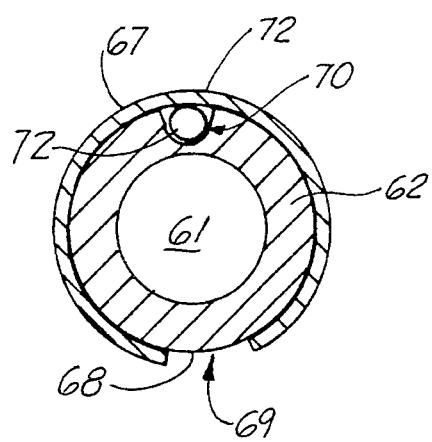

Locking collar 67 is generally cylindrically shaped, and affixes to a smaller diameter cylindrically shaped section 68 of larger cylindrical section 62. Locking collar 67 is in the form of an elongated hollow cylinder having a longitudinal slot 69. The slot 69 can be aligned with probe 72 (see FIG. 15). In this position, the probe can pivot about pivot 71, allowing the probe to move away from the central longitudinal axis of bore 61 as shown in FIG. 14. Probe 72 has a configuration similar to the configuration of the probes of the embodiments shown in FIGS. 1–12.

The locking collar 67 is a regular cylinder which rotates around instrument body 58 and more particularly around the larger cylindrical section 62 thereof. Locking is obtained by simply rotating the collar 67. The probe 72 is "buried" in the thickness of the drill sleeve, occupying a position in longitudinally extending recess 70. In locking position as in open position, the collar 67 does not protrude beyond instrument body 58 as shown in FIGS. 13–16.

The hinged probe 72 pivots about pivot 71 when the guide 57 is removed from the patient. The hinged probe 72 prevents the tip 73 from catching the lip of the iliac crest when the guide apparatus 57 is removed from the patient.

The following table lists the part numbers and part descriptions as used herein and in the drawings attached hereto.

PARTS LIST

| Part Number | Description |
| --- | --- |
| 10 | pelvic drill guide apparatus |
| 11 | instrument body |
| 12 | barrel |
| 13 | proximal end |
| 14 | distal end |
| 15 | cylindrical bore |
| 15A | cylindrical bore |
| 16 | cylindrical portion |
| 17 | cylindrical portion |
| 18 | teeth |
| 19 | enlarged section |
| 20 | handle |
| 21 | gripping surface |
| 22 | connection |
| 23 | arm |
| 24 | probe |
| 25 | connection |
| 26 | straight section |
| 27 | bend |
| 28 | straight section |
| 29 | bend |
| 30 | straight section |
| 31 | bend |
| 32 | straight section |
| 33 | pointed tip |
| 34 | drill |
| 35 | larger cylindrical portion |
| 36 | annular shoulder |
| 37 | smaller cylindrical cutting portion |
| 38 | cutting tip |
| 39 | tool flats |
| 40 | pin |
| 41 | cylindrical unthreaded section |
| 42 | arrow |
| 43 | threaded section |
| 44 | cutting tip |
| 45 | inner table |
| 46 | pilot hole |
| 47 | iliac crest |
| 48 | arrow |
| 49 | arrow |
| 50 | axis |
| 51 | interchangeable sleeve - large bore |
| 52 | internal sleeve bore (large) |
| 52A | cylindrical collar - large bore |
| 53 | interchangeable sleeve bore - small bore |
| 54 | internal sleeve bore (small) |
| 54A | cylindrical collar - small bore |
| 55 | enlarged diameter collar |
| 57 | drill guide apparatus |
| 58 | instrument body |
| 59 | distal end |
| 60 | proximal end |
| 61 | bore |
| 62 | larger cylindrical section |
| 63 | smaller cylindrical section |
| 64 | teeth |
| 65 | handle |
| 66 | strut |
| 67 | locking collar |
| 68 | smaller diameter section |
| 69 | slot |
| 70 | longitudinal recess |
| 71 | pivot |
| 72 | probe |
| 73 | tip |
| 75 | conventional external fixation system |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A pelvic pin guide apparatus comprising:
   a) an elongated instrument body;
   b) the instrument body including a tubular barrel with an outer surface and an inner central longitudinal bore;
   c) a handle that extends laterally from the outer surface of the barrel for gripping and manipulating the instrument body during surgical placement of holes in the patient's pelvis;
   d) a pointer extending from the proximate end of the barrel and along a line that is generally parallel to and offset from the central longitudinal axis of the barrel bore, the pointer having a sharp distal tip that can be used by the surgeon to track the surface of the patient's pelvic cortex during a drilling of surgically placed holes that are drilled by the surgeon into the patient's pelvis;
   e) the pointer distal tip being offset a few millimeters from a line that coincides with the central longitudinal axis of the barrel, the pointer distal tip being spaced away from the distal end of the barrel along a line that coincides with the central longitudinal axis of the barrel;
   f) the bore being sized and shaped to hold a generally cylindrically shaped drill and wherein the pointer distal tip is positioned adjacent the outer surface of the drill when the drill is extended through the barrel to the pointer.

2. A pelvic pin guide apparatus for positioning a drill bit and corresponding pelvic pin in an iliac bone comprising:
   a) an instrument body that includes a handle for gripping and manipulating the instrument body during surgical placement of holes in the patient's pelvis;
   b) the instrument body having a tubular barrel with a central longitudinal bore;
   c) pointer means extending from the proximate end of the barrel and along a line that is generally parallel to and offset from the central longitudinal axis of the bore, for subcutaneously tracking the surface of the patient's pelvic cortex during a drilling of surgically placed holes;
   d) the pointer means being an elongated member integral with and affixed to an outer surface portion of the barrel;
   e) the pointer means including a distal tip portion that is offset a few millimeters from the central longitudinal axis of the barrel and spaced away from the distal end of the barrel along a line that coincides with the central longitudinal axis of the barrel;
   f) the bore being sized and shaped to hold a generally cylindrically shaped drill and wherein the pointer is positioned adjacent the outer surface of the drill when the drill is extended through the barrel to the pointer.

3. The apparatus of claim 2 further comprising a sleeve that removably fits the bore of the barrel, the sleeve having a sleeve bore that conforms to the outer surface of the drill during use.

4. The apparatus of claim 2 wherein the handle includes a strut that affixes to the outer surface of the barrel and extends laterally away from the barrel.

5. The apparatus of claim 3 wherein the handle includes a strut that affixes to the outer surface of the barrel and extends laterally away from the barrel.

6. The apparatus of claim 2 further comprising a distal end portion of the barrel with means for gripping tissue at the patient's pelvis when the surgeon is preparing to place surgically formed holes in the patient's pelvis.

7. The apparatus of claim 6 wherein the gripping means comprises at least one tooth that extends from the distal end of the barrel.

8. The apparatus of claim 2 wherein the handle and pointer means are spaced circumferentially about the barrel outer surface.

9. The apparatus of claim 8 wherein the handle and pointer means are spaced circumferentially about one hundred eighty degrees about the barrel outer surface.

10. A method of inserting pins into the iliac bone of a patient comprising the steps of:
    a) forming an incision on a side of the patient's pelvis just proximal to the axis and exposing the iliac crest;
    b) elevating the muscle medial to the iliac crest;
    c) pushing the tip of a drill guide along the inner table of the pelvis;
    d) positioning the guide on the pelvic rim so that pins can be inserted in an anteroposterior direction;
    e) placing a drill in the drill guide;
    f) using the drill guide to track the drill into the patient's pelvis through the cortex of the iliac crest into the iliac bone along a path that prevents inadvertent penetration of either cortex from occurring.

11. The method of claim 10 wherein in step "f" a plurality of drilled openings are formed at spaced apart locations.

12. The method of claim 11 wherein in step e the drill occupies a position within a bore of the drill guide and in step "c" the guide has a pointer that extends to the distal end of the drill guide.

13. The method of claim 10 wherein in step "c" the drill guide is manually placed by the surgeon.

14. The method of claim 13 further comprising the step of placing a plurality of pins respectively in the drilled openings.

15. The method of claim 14 further comprising the step of connection the pins with an external fixation system.

* * * * *